United States Patent [19]

Chen et al.

[11] 4,192,785

[45] Mar. 11, 1980

[54] OSTOMY ADHESIVE

[75] Inventors: James L. Chen, East Brunswick; Rudolfo D. Cilento, North Brunswick; John A. Hill, New Brunswick; Anthony L. La Via, East Brunswick, all of N.J.

[73] Assignee: E. R. Squibb & Sons, Inc., Princeton, N.J.

[21] Appl. No.: 804,673

[22] Filed: Jun. 8, 1977

[51] Int. Cl.$^2$ .............................................. C08L 3/02
[52] U.S. Cl. .......................... 260/17.4 GC; 128/283; 260/17 R; 260/17.4 BB; 260/17.4 CL; 260/17.4 ST
[58] Field of Search ..... 260/17 R, 17.4 CL, 17.4 GC, 260/17.4 BB; 128/283

[56] References Cited

U.S. PATENT DOCUMENTS

| 3,379,662 | 4/1968 | Bramble et al. | 260/17.4 BB |
|---|---|---|---|
| 3,490,444 | 1/1970 | Larson | 260/17.4 BB |
| 3,897,780 | 8/1975 | Trousil | 128/283 |
| 3,908,658 | 9/1975 | Marsan | 128/283 |
| 3,980,084 | 9/1976 | Kross | 128/283 |
| 4,095,599 | 6/1978 | Simonet-Haibe | 128/283 |

*Primary Examiner*—Edward M. Woodberry
*Attorney, Agent, or Firm*—Lawrence S. Levinson; Stephen B. Davis

[57] ABSTRACT

An adhesive composition adapted for use with an ostomy appliance consisting of a mixture of a hydrocolloid gum, a pressure sensitive adhesive, and a cohesive strengthening agent. The cohesive strengthening agent is either an inert natural or synthetic fibrous material, finely divided cellulose, a cross-linked dextran, a cross-linked carboxymethylcellulose, or a starch-acrylonitrile graft copolymer.

7 Claims, No Drawings

OSTOMY ADHESIVE

BACKGROUND OF THE INVENTION

Major abdominal surgery for a number of diseases involving different parts of the gastro-intestinal and urinary tract can result in a patient being left with an abdominal stoma. The three most common types of abdominal stoma are the colostomy, the ileostomy, and the ileal conduit. In the case of an ileostomy, ileal conduit, and many colostomy operations, the patient is unable to control the passage of bodily waste material and must rely upon an appliance attached to their body to collect this material.

Several systems have been employed in the past for this purpose. Colostomates normally employ a disposable appliance which is either a one-piece or two-piece unit. The term disposable refers to the fact that the pouch or bag portion of the unit can be disposed of after a single use. A closed end pouch sealed along all of its edges with only an opening for the stoma is suitable for this purpose. The two-piece disposable unit consists of such a bag suspended from a reusable mounting ring that is supported by a belt. The one-piece disposable unit can be a disposable bag having an adhesive face plate which is attached directly to body as shown in U.S. Pat. No. 3,055,368, a disposable bag having a mounting gasket which is supported by a belt and can include a sealing ring of karaya and glycerol as shown in U.S. Pat. No. 3,302,647, or a disposable bag supported by a sealing ring of karaya and glycerol, an adhesive ring, and a belt as shown in U.S. Pat. No. 3,351,061.

Persons having an ileostomy or urinary stoma normally employ a permanent (i.e., reusable) system or a semi-permanent system. This refers to the fact that the waste collecting bag or pouch has a valve or other type of closure means at the bottom. This permits the unit to remain on the body for several days. Again, these systems are available as either a one-piece or two-piece unit.

The one-piece reusable unit consists of a bag having a bottom valve or other closure means and a permanently bonded rubber or plastic faceplate. The faceplate has a centrally located opening for the stoma and can be attached directly to the body by means of latex cement or a double sided pressure sensitive adhesive disk. It is also common to adhesively attach the faceplate to a skin barrier which fits around the stoma rather than directly to the skin. For added security, a pressure plate having a belt attachment and a plastic or metal ring that fits between the faceplate and the bag can be employed. After several days the adhesive bond between the faceplate and the body or skin barrier will weaken and the unit will be removed. The unit is cleaned and residual adhesive is removed from the faceplate so that it can be reapplied. Eventually, the entire unit except for the pressure plate will have to be discarded due to erosion or odor build-up in the bag.

One-piece semi-permanent units for use with an ileostomy stoma having a karaya sealing ring bonded to the faceplate are commercially available.

The two-piece reusable unit consists of a rubber flange having an opening for the stoma which is adhesively attached directly to the body or to a skin barrier and a separate bag having a bottom valve or other closure means which fits tightly over the flange.

Chen in U.S. Pat. No. 3,339,546 describes a bandage having an adhesive layer consisting of a mixture of gelatin, pectin, sodium carboxymethylcellulose, and polyisobutylene and a water insoluble polyethylene film. This bandage is currently employed as a skin barrier by ostomates and is also available with a permanently attached flange.

Other commercially available skin barriers contain a cloth mesh layer or polyethylene web sandwiched between two adhesive layers. The adhesive layers comprise a conventional pressure sensitive adhesive and a hydrocolloid.

Further attempts have been made to develop ostomy sealing washers of materials other than the karaya-glycerol gel described by Marsan in U.S. Pat. No. 3,302,647. For example, Pratt in U.S. Pat. No. 3,612,053 describes an ostomy sealing washer formed from an oil-extended block copolymer having a water activatable adhesive on one surface, Marsan in U.S. Pat. Nos. 3,712,304 and 3,799,166 describes an ostomy seal made from starch and gelatinized starch cross-linked with glyoxal, Marsan in U.S. Pat. No. 3,878,847 describes a thin membrane that contacts the stoma, Marsan in U.S. Pat. No. 3,908,658 describes an ostomy seal formed from a gel of mineral oil, styreneisobutylene copolymer and an ethylene-vinyl acetate copolymer, and Kross in U.S. Pat. Nos. 3,877,431 and 3,980,084 describes ostomy seals formed from polymeric materials.

SUMMARY OF THE INVENTION

This invention is directed to an improved adhesive composition which is particularly adapted to be used in the ostomy field.

The adhesive composition consists of a mixture of a hydrocolloid gum, a pressure sensitive adhesive, and an agent which increases the cohesive strength of the composition. The cohesive strengthening agent is either an inert natural or synthetic fibrous material, a finely divided purified wood cellulose, a cross-linked dextran, a cross-linked carboxymethylcellulose, or a starch-acrylonitrile graft copolymer.

DETAILED DESCRIPTION

For an adhesive composition to be useful in the ostomy field it must possess several attributes. Since the composition is contacting the body around the stoma it must not contain ingredients which will irritate this already sensitive area of skin.

When the adhesive composition is employed as a skin barrier it must be capable of supporting the weight or the attached one-piece or two-piece appliance and yet permit removal of the appliance for disposal or cleaning without also removing the barrier from the skin. It is desirable from both an economic and medical point of view to have a skin barrier which can remain in place for a week or longer.

The adhesive composition whether used as a skin barrier, formed into sealing rings, or applied directly onto the faceplate of a one-piece appliance or the flange element of a two-piece appliance must resist erosion caused by the leakage of effluent from the stoma. Particularly, with a urinary stoma, ileostomy, or "wet" colostomy the effluent is highly caustic and can erode the adhesive causing failure of the bandage and the partially dissolved adhesive material can flow into the bag blocking the bottom drain valve. Also, erosion of the adhesive permits this corrosive effluent to contact the skin causing serious irritation.

As discussed above, previous attempts to develop an adhesive composition having these properties included the incorporation of various hydrocolloid gum materials into the adhesive composition. It was felt that these hydrocolloid materials would absorb moisture such as perspiration and provide wet adhesion for the composition. It was also known that the cohesive strength of the adhesive composition was an important factor. This strengthening was provided, as discussed above, by the presence of an outer polymeric film or a cloth mesh or polyethylene web sandwiched within the adhesive composition.

It has now been discovered that an adhesive composition having the properties of long duration of adhesion as well as cohesive strength can be obtained by employing certain hydrocolloid gums, pressure sensitive adhesives, and a cohesive strengthening agent. It has been found that certain hydrocolloid gums while possessing the ability to absorb surface moisture such as perspiration, in fact, are not suitable for use in the composition since they swell too rapidly and turn into a soft gelatinous mass. This swelling and loss of consistency causes the adhesive composition to erode the disintegrate.

Thus, the hydrocolloid gum component of the adhesive composition should have a large capacity to absorb moisture, should provide wet adhesion, and should also hydrate and swell at a relatively slow rate so as not to cause disintegration of the adhesive composition. Guar gum, locust bean gum, and mixtures thereof have been found to be suitable with guar being preferred and such gums can be present at from about 15% to about 40% by weight of the adhesive composition.

An additional gum substance having soothing or healing properties can be included within the adhesive composition. Pectin, gum karaya, and mixtures thereof have been found to be suitable with pectin being preferred and can be present at from 0% to about 25% by weight of the adhesive composition provided that the total amount of gums within the adhesive composition is from about 25% to about 55% by weight.

The pressure sensitive adhesive component of the composition provides dry adhesion and holds the entire composition together. Various natural or synthetic viscous substances either possessing dry tack by themselves or developing such tack upon the addition of a plasticizer such as natural rubber, silicone rubber, acrylonitrile rubber, polyurethane rubber, polyisobutylenes, etc., are suitable for this purpose. Low molecular weight polyisobutylenes having a viscosity average molecular weight of from about 36,000 to about 58,000 (Flory) are preferred. Such polyisobutylenes are commercially available under the trademark Vistanex from Exxon Co. as grades LM-MS and LM-MH. Optionally, in order to increase the elasticity and tear resistance of the adhesive composition elastomeric polymers such as medium molecular weight polyisobutylenes having a viscosity average molecular weight of from about 1,150,000 to 1,600,000 (Florey) or butyl rubber which is a copolymer of isobutylene with a minor amount of isoprene having a viscosity average molecular weight of from about 300,000 to about 450,000 (Florey) can be added. Butyl rubber having a viscosity average molecular weight of about 425,000 (commercially available as grade 077) is preferred. The elastomer can be added in amounts of up to about 30% by weight of the pressure sensitive adhesive. The pressure sensitive adhesive and the optionally added elastomer together can be from about 40% to about 60% by weight of the adhesive composition. Preferably, the low molecular weight polyisobutylene pressure sensitive adhesive and the higher molecular weight butyl rubber elastomer are employed in a ratio of from about 3 to 1 to about 5 to 1 on a weight basis, 4 to 1 being most preferred, and the combination is present at from about 45% to about 55% by weight of the total adhesive composition.

The cohesive strengthening agent functions in the adhesive composition by increasing resistance to tearing, decreasing the tendency to erode and disintegrate by absorbing moisture and thus controlling the swelling of the hydrocolloid gums, and controlling oozing. Oozing is due to the cold-flow of the polyisobutylene and occurs when the adhesive composition is stored for several months. Oozing is increased when the adhesive composition is heated or gamma irradiated.

Materials suitable for use as the cohesive strengthening agent include natural or synthetic inert fibrous materials such as cotton and Dacron, finely divided cellulose materials including purified wood cellulose such as that available commercially under the trademark Solka-Floc and microcrystalline cellulose such as that available commercially under the name Avicel, finely divided substantially water insoluble cross-linked dextran such as that available commercially under the trademark Sephadex, finely divided substantially water insoluble cross-linked sodium carboxymethylcellulose such as that available commercially under the trademark Aqualon or that described in U.S. Pat. No. 3,589,364 and available commercially from The Buckeye Cellulose Corp., and a finely divided substantially water insoluble starch-acrylonitrile graft copolymer such as that described in U.S. Pat. No. 3,661,815 and commercially available from the Grain Processing Corp. The fibrous material is employed at from about 2% to about 12% by weight of the adhesive composition and the cellulose, cross-linked dextran, cross-linked sodium carboxymethylcellulose, or starch-acrylonitrile graft copolymer are employed at from about 10% to about 30% by weight of the adhesive composition. Cotton and purified wood cellulose are the preferred cohesive strengtheners.

Small amounts, i.e., less than 5% by weight of the adhesive composition, of other ingredients can be also included. For example, a plasticizer such as mineral oil, an antioxidant such as butylated hydroxyanisole, a deodorant or perfume agent.

The adhesive composition is prepared by forming a homogeneous dispersion of the pressure sensitive adhesive component and the elastomer with a heavy duty mixer, e.g. a kneader mixer or sigma blade mixer. The hydrocolloid gums, cohesive strengthening agent, and any other optional ingredients are added and mixing is continued until a homogeneous dough is formed. Alternatively, the elastomer is first broken down by mixing for several minutes, a portion of the pressure sensitive adhesive and other ingredients are added and mixing continued until a homogeneous mass is formed. The balance of the pressure sensitive adhesive is then added and the mixing continued until a homogeneous dough is formed. This dough can then be extruded and shaped as desired.

If desired a thin continuous or discontinuous film of polymeric material such as polyethylene, polyurethane, PVC, PVDC, etc. can be laminated onto one side of the adhesive material as taught in U.S. Pat. No. 3,339,546. The film is present at from about 1.0 to about 10.0 mils. thickness and will, of course, increase the cohesiveness of the adhesive composition. The exposed side of the adhesive composition or both sides if the film is omitted is covered with a piece of silicone coated release paper. A flange can be attached directly to this skin barrier for use by those ostomates who prefer a two-piece system.

The improved adhesive composition can also be shaped so as to be used as an ostomy sealing washer.

The improved adhesive composition either with or without the outer polymeric film layer can also be bonded to the faceplate or mounting gasket of an ostomy bag as in U.S. Pat. Nos. 3,302,647 and 3,351,061 or the improved adhesive composition without the outer polymeric layer can be applied directly to as ostomy bag as in U.S. Pat. No. 3,055,368.

While the adhesive composition of this invention has been particularly described for use in the ostomy field, it is also useful for related medicinal purposes. For example, the adhesive composition can be employed to affix various devices to the body such as a catheter, an electronic probe, a wound drainage system as taught in U.S. Pat. Nos. 3,568,675 to Harvey and 3,954,105 to Nordby or can be applied directly to a subcutaneous ulcer.

The adhesive composition of this invention can be sterilized by means of gamma radiation.

Preferred adhesive compositions within the scope of this invention comprise on a weight basis from about 2% to about 12% cotton or from about 10 to about 30% finely divided purified wood cellulose as the cohesive strengthening agent; from about 15% to about 40% guar gum; from about 0% to about 25% pectin provided that when the cohesive strengthening agent is cotton the guar gum and pectin combined are from about 35% to about 55% and when the cohesive strengthening agent is wood cellulose the guar gum and pectin combined are from about 20% to about 45%; and from about 45% to about 55% of the mixture of low molecular weight polyisobutylene and butyl rubber wherein the ratio of low molecular weight polyisobutylene to butyl rubber is about 4 to 1 on a weight basis.

The following examples are illustrative of the invention. Other suitable adhesive composition can be obtained by minor variations in the amounts of ingredients employed.

EXAMPLE 1

This example is directed to preparing an adhesive having the following composition:

| Ingredient | Percent by weight |
| --- | --- |
| Polyisobutylene of a viscosity average molecular weight (Flory) of 36,000 to 45,000 (Vistanex LM-MS of Exxon) | 40 |
| Butyl rubber of a viscosity average molecular weight (Flory) of 425,000 (Exxon grade 077) | 10 |
| Guar gum of high grade extra fine powder (Jaguar A-40-F of Stein Hall Co.) | 30 |
| Finely divided purified wood cellulose (Solka Floc BW-100 of Brown Co.) | 20 |
| | 100 |

2 kg. of butyl rubber is broken down by mixing in a kneader mixer for two to five minutes. 4 kg. of the low molecular weight polyisobutylene is added and mixed with the butyl rubber for two to five minutes. 6 kg. of guar gum and 4 kg. of the finely divided purified wood cellulose are combined in a powder mixer and the resulting powder is added to the polyisobutylene-butyl rubber mixture. Mixing of the ingredients is continued until a homogeneous mass is formed with the polyisobutylene and butyl rubber completely interdispersed (about 10 to 20 minutes). The remaining 4 kg. of the low molecular weight polyisobutylene is added and mixing is continued until a homogeneous dough is formed (about 10 to 20 minutes).

This dough mass while hot and soft is extruded and flattened. A sheet of polyethylene of 1.5 mils thickness is pressed over one side and silicone coated release paper on the other. The resultant mat is cut into the desired shape.

EXAMPLES 2–26

Following the procedure of example 1 but employing the following ingredients on a percent weight basis other adhesive compositions within the scope of the invention are prepared.

| Ex. | Polyisobutylenes (4:1 ratio of Vistenex LM-MS and butyl rubber grade 077) | Guar gum | Locust bean gum | Pectin | Karaya | Purified wood cellulose (Solka-floc) | Microcrystalline cellulose (Avicel) | Cross-linked dextran (Sepadex CM-C50) |
| --- | --- | --- | --- | --- | --- | --- | --- | --- |
| 2 | 50% | 20% | — | — | — | 30% | — | — |
| 3 | 50% | 40% | — | — | — | 10% | — | — |
| 4 | 50% | 35% | — | — | — | 15% | — | — |
| 5 | 45% | 35% | — | — | — | 20% | — | — |
| 6 | 50% | 20% | — | 10% | — | 20% | — | — |
| 7 | 40% | 30% | — | 20% | — | 10% | — | — |
| 8 | 50% | 15% | — | 15% | — | 20% | — | — |
| 9 | 50% | 25% | — | 10% | — | 15% | — | — |
| 10 | 40% | 25% | — | — | 25% | 10% | — | — |
| 11 | 50% | 35% | — | — | — | — | — | 15% |
| 12 | 45% | 35% | — | — | — | — | — | 20% |
| 13 | 45% | 35% | — | — | — | — | 20% | — |
| 14 | 50% | — | 30% | — | — | 20% | — | — |
| 15 | 50% | — | 20% | — | — | 30% | — | — |
| 16 | 50% | 20% | 10% | — | — | 20% | — | — |
| 17 | 40% | 20% | — | 15% | 15% | 10% | — | — |

-continued

| Ex. | Polyisobutylenes (4:1 ratio of Vistanex LM-MS and butyl rubber grade 077) | Guar gum | Locust bean gum | Pectin | Karaya | Cross-linked sodium carboxymethyl-cellulose (Hercules Aqualon R or Buckeye Cellulose Corp. CLD) | Starch-acrylonitrile graft copolymer (Grain Processing Corp. Polymer 35-A-100) |
|---|---|---|---|---|---|---|---|
| 18 | 60% | 25% | — | — | — | 15% | — |
| 19 | 45% | — | 35% | — | — | 20% | — |
| 20 | 50% | — | 20% | 10% | — | 20% | — |
| 21 | 50% | 35% | — | — | — | 15% | — |
| 22 | 45% | 35% | — | — | — | 20% | — |
| 23 | 40% | 25% | — | 25% | — | 10% | — |
| 24 | 50% | 35% | — | — | — | — | 15% |
| 25 | 45% | 35% | — | — | — | — | 20% |
| 26 | 40% | — | 25% | 25% | — | — | 10% |

EXAMPLE 27

This example is directed to preparing an adhesive having the following composition.

| Ingredient | Percent by weight |
|---|---|
| Polyisobutylene of a viscosity average molecular weight of 36,000 to 45,000 (Flory) (Vistanex LM-MS of Exxon) | 38.0 |
| Butyl rubber of a viscosity average molecular weight (Flory) of 425,000 (Exxon Grade 077) | 9.5 |
| Guar gum of high grade, extra fine powder (Jaguar A-40-F of Stein Hall Co.) | 28.5 |
| Pectin | 19.0 |
| Cotton | 5.0 |
| | 100.0 |

1.9 kg. of butyl rubber is broken down by mixing in a kneader mixer for two to five minutes. 3.8 kg. of the low molecular weight polyisobutylene is added and mixed with the butyl rubber for two to five minutes. 5.7 kg. of guar gum and 3.8 kg. of pectin are combined in a powder mixer and the resulting powder is added to the low molecular weight polyisobutylene-butyl rubber mixture followed by the addition of 1 kg. of cotton. Mixing of the ingredients is continued until a homogeneous mass is formed with the polyisobutylene and butyl rubber completely interdispersed (about 10 to 20 minutes). The remaining 3.8 kg. of low molecular weight polyisobutylene is added and mixing continued until a homogeneous dough is formed (about 10 to 20 minutes).

This dough mass can then be extruded and laminated with a sheet of polyethylene as set forth in Example 1.

EXAMPLES 28 TO 36

Following the procedure of example 27 but employing the following ingredients on a percent weight basis other adhesive compositions within the scope of the invention are prepared.

| Ex. | Polyisobutylene (4:1 ratio of Vistenex LM-MS and butyl rubber grade 077) | Guar gum | Locust bean gum | Pectin | Karaya | Cotton |
|---|---|---|---|---|---|---|
| 28 | 50% | 20% | — | 20% | — | 10% |
| 29 | 47.5% | — | 28.5% | 19% | — | 5% |
| 30 | 47.5% | 28.5% | — | — | 19% | 5% |
| 31 | 50% | 30% | — | 10% | — | 10% |
| 32 | 55% | 23% | 10% | — | — | 12% |
| 33 | 50% | 25% | — | 10% | 10% | 5% |
| 34 | 60% | 20% | — | 8% | — | 12% |
| 35 | 40% | 34% | — | 24% | — | 2% |
| 36 | 50% | 30% | — | 10% | — | 10% |

What is claimed is:

1. An adhesive composition for medicinal purposes consisting essentially of a substantially homogenous mixture on a percent weight basis of from about 15% to about 40% of guar gum, locust bean gum, or mixtures thereof; from 0% to about 25% of pectin, gum karaya, or mixtures thereof provided that the total amount of guar gum, locust bean gum, gum karaya and pectin is from about 20% to about 55%; from about 40% to about 60% of a mixture of a low molecular weight polyisobutylene having a viscosity average molecular weight of from about 36,000 to about 58,000 on the Flory scale and butyl rubber having a viscosity average molecular weight of from about 300,000 to about 450,000 on the Flory scale, said polyisobutylene and said butyl rubber combined in a ratio of from about 3 to 1 to about 5 to 1 on a weight basis; and as a cohesive strengthening agent from about 2% to about 12% of an inert natural or synthetic fibrous material or from about 10% to about 30% of a finely divided cellulose, a finely divided substantially water insoluble cross-linked dextran, a finely divided substantially water insoluble cross-linked sodium carboxymethylcellulose, or a finely divided substantially water insoluble starch-acrylonitrile graft polymer.

2. The composition of claim 1 wherein the cohesive strengthening agent is from about 2% to about 12% cotton.

3. The composition of claim 2 comprising from about 15% to about 40% guar gum; from 0% to 25% pectin provided that the total amount of guar gum and pectin is from about 35% to about 55%; and from about 45% to about 55% of the mixture of said low molecular weight polyisobutylene and said butyl rubber wherein the ratio of low molecular weight polyisobutylene to butyl rubber is about 4 to 1 on a weight basis.

4. The composition of claim 3 comprising about 5% cottom, about 28.5% guar gum, about 19% pectin, about 47.5% of a 4 to 1 mixture of polyisobutylene of a viscosity average molecular weight of about 36,000 to about 45,000 on the Flory scale and butyl rubber of a viscosity average molecular weight of about 425,000 on the Flory scale.

5. The composition of claim 1 wherein the cohesive strengthening agent is from about 10% to about 30% finely divided purified wood cellulose.

6. The composition of claim 5 comprising from about 15% to about 40% guar gum; from 0% to 25% pectin provided that the total amount of guar gum and pectin is from about 20% to 45%; and from about 45% to about 55% of said mixture of low molecular weight polyisobutylene and said butyl rubber wherein the ratio of low molecular weight polyisobutylene to butyl rubber is about 4 to 1 on a weight basis.

7. The composition of claim 6 comprising about 20% finely divided purified wood cellulose, about 30% guar gum, and about 50% of a 4 to 1 mixture of polyisobutylene of a viscosity average molecular weight of about 36,000 to about 45,000 on the Flory scale and butyl rubber of a viscosity average molecular weight or about 425,000 on the Flory scale.

* * * * *

UNITED STATES PATENT AND TRADEMARK OFFICE
CERTIFICATE OF CORRECTION

PATENT NO. : 4,192,785
DATED : March 11, 1980
INVENTOR(S) : James L. Chen, Rudolfo D. Cilento, John A. Hill, Anthony L. LaVia It is certified that error appears in the above—identified patent and that said Letters Patent is hereby corrected as shown below:

Col. 3, line 23, "the" (second occurrence) should be -- and --.
Col. 8, line 67, "cottom" should be -- cotton --.

Signed and Sealed this

Twenty-first Day of October 1980

[SEAL]

Attest:

SIDNEY A. DIAMOND

Attesting Officer

Commissioner of Patents and Trademarks